United States Patent [19]

Yee

[11] 4,243,326
[45] Jan. 6, 1981

[54] NICKEL ANALYSIS DEVICE

[75] Inventor: Tin B. Yee, Huntsville, Ala.

[73] Assignee: The United States of America as represented by the Secretary of the Army, Washington, D.C.

[21] Appl. No.: 81,998

[22] Filed: Oct. 4, 1979

[51] Int. Cl.$^3$ .............................................. G01N 21/27
[52] U.S. Cl. ...................................... 356/414; 422/68
[58] Field of Search ...................... 356/409, 414, 412; 422/68

[56] References Cited

U.S. PATENT DOCUMENTS

| | | | |
|---|---|---|---|
| 3,030,192 | 4/1962 | Schneider, Jr. | 356/412 X |
| 3,440,016 | 4/1969 | Serfass | 356/412 X |
| 3,874,794 | 4/1975 | Schmitt et al. | 356/414 X |

*Primary Examiner*—F. L. Evans
*Attorney, Agent, or Firm*—Nathan Edelberg; Robert P. Gibson; Jack W. Voigt

[57] ABSTRACT

Disclosed is a device for use in the colorimetric analysis of nickel in a chemical plating solution. The device employs an automatic measuring system which includes a first automatic measuring system which comprises a means for transferring a chemical plating solution to be analyzed from a container to a first volumetric cup disposed to receive the solution into an inner section of the cup which is filled to overflowing into an outer section of the first volumetric cup. The outer section of the first volumetric cup has means for draining solution to the container. The first volumetric cup inner section is provided with drain means at bottom for draining the plating solution sample into an absorption cell. A second automatic measuring system is provided which comprises a means for transferring a standardized ammonium hydroxide solution by gravity flow from a second container to a second volumetric cup having an inner and outer section. The second volumetric cup inner section is provided with drain means at bottom for draining the standardized ammonium hydroxide solution into an absorption cell. A means for flow control is connected between the second container and inner section of the second volumetric cup. The outer section is disposed for receiving any overflow from the inner section and has means connecting the outer section to a second container for receiving any overflow. The outer section of the second volumetric cup is provided with means for draining the standardized hydroxide solution into a suitable container for ammonium hydroxide. After mixing the plating solution sample and ammonium hydroxide in the absorption cell a blue to violet colored complex is formed. A colorimeter employing a yellow filter (near 580 millimicrons wavelength) or a green filter (near 525 millimicrons wavelength) and a detector is employed to measure the transmittance or the absorption of a monochromatic light that is passed through the colored complex. The detector value is amplified and compared with a detector value measured on a standard sample as corrected by a blank sample to determine the nickel content of the chemical plating solution.

2 Claims, 1 Drawing Figure

U.S. Patent  Jan. 6, 1981  4,243,326
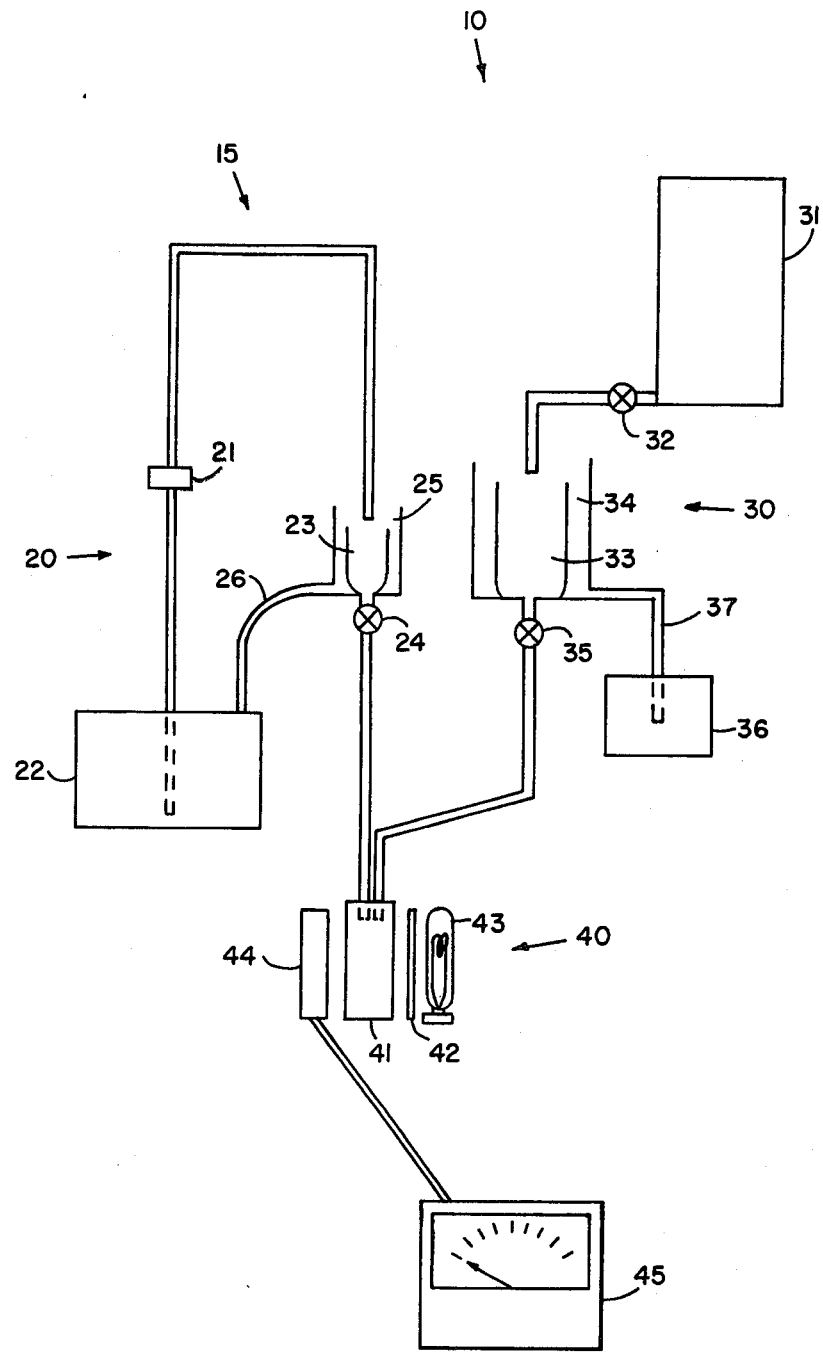

NICKEL ANALYSIS DEVICE

DEDICATORY CLAUSE

The invention described herein may be manufactured, used, and licensed by or for the Government for governmental purposes without the payment to me of any royalties thereon.

BACKGROUND OF THE INVENTION

Chemical plating solutions are required to be analyzed to determine that the proper concentration of plating solution chemicals and metal element are present. Some plating solutions require more precise control than others. For example a chemical plating solution that is used for nickel plating of printed electrical circuit boards requires very close control. The nickel content present in the chemical plating solution must be known while plating. If there is more or less nickel than the specified concentration, undesirable electrical circuit boards will result.

At present, when an operator wants to know the nickel content in a plating solution, he will take a sample of the plating solution and carry it to a set-up in the plating room or to an analytical laboratory to be analyzed by a chemist. A conventional method that is generally used for the analysis of nickel in the plating solution is the ethylenediaminetetraacetate (EDTA) titration method. Such a method is time consuming.

A less time consuming and a very accurate method for determining nickel would be advantageous for circuit board plating industry. Therefore, an object of this invention is to provide a simple, inexpensive, and dependable analytical device for the determination of nickel in the chemical plating solution. Another object of this invention is to provide a fast chemical method for the analysis of nickel in the chemical plating solution that can be carried out in a matter of a few minutes. Yet another object of this invention is to provide a simple device so that an unskilled technician can be trained to operate it.

SUMMARY OF THE INVENTION

The nickel analysis device of this invention is comprised of a first automatic measuring system, a second automatic measuring system, and a colorimetric measurement system. The first automatic measuring system is provided with a means for transferring a sample of plating solution to be analyzed from a container to a first volumetric cup disposed to receive the solution into an inner section of the cup which is filled to overflowing into an outer section of the first volumetric cup. The outer section of the first volumetric cup has means for draining solution to a container. The second automatic measuring system is of similar design to first automatic measuring system, but the second automatic measuring system is designed to measure and transfer a standard ammonium hydroxide solution. The first and second automatic measuring system delivers the predetermined volumes of plating solution and ammonium hydroxide solution into an absorption cell wherein a colored complex is formed. A colorimetric measurement system is employed to measure the transmittance of a monochromatic light which is proportionate to the nickel of the colored complex. A monochromatic light is passed through the colored complex to a detector and amplifier means which determines a detector value proportionate to the transmittance or absorption of the light. The detector value is amplified and compared with a detector value measured on a standard sample treated similarly and as corrected by a blank sample to determine the nickel content of the chemical plating solution.

BRIEF DESCRIPTION OF THE DRAWING

The FIGURE of the drawing depicts a schematic configuration of the nickel analysis device 10 of this invention which employs an automatic measuring system 15 which is comprised of a first automatic measuring system 20 and a second automatic measuring system 30 in working arrangement with a colorimeter measurement system 40.

DESCRIPTION OF THE PREFERRED EMBODIMENT

In further reference to the drawing, the nickel analysis device 10 is comprised of a first automatic measuring system 20 which includes pumping means 21 for transferring a sample of plating solution from a plating tank container 22 to a first volumetric cup inner section 23 fitted with drain means 24 and designed to overflow into a first volumetric cup outer section 25 fitted with drain means 26 for returning excess solution to container 22. The drain means 24 includes a stopcock and tubing which serves to drain the predetermined volume of sample into a rectangular absorption cell 41. The nickel analysis device is comprised of a second automatic measuring system 30 which includes similarly designed components as said first automatic measuring system wherein a first container for ammonium hydroxide depicted as 31 is fitted with a means 32 for transferring a standard ammonium hydroxide solution to second volumetric cup inner section 33 fitted with drain means 35 comprising a stopcock and tubing which serves to drain the predetermined volume of ammonium hydroxide solution, into absorption cell 41. The inner cup is designed to overflow into a second volumetric outer cup 34. The outer section 34 of the second volumetric cup is depicted with drain means 37 for automatically draining ammonium hydroxide solution into an overflow container 36. The plating solution sample is thoroughly mixed with the ammonium hydroxide in the absorption cell 41 to produce a blue to violet colored complex. The colorimeter measurement system 40 is comprised of said rectangular absorption cell 41, a tungsten lamp 43 which produces a light to pass through a yellow filter 42 (near 580 millimicrons wavelength for maximum absorption) or a green filter (near 525 millimicrons wavelength) to yield a monochromatic light by the test solution in the absorption cell 41, and a detector and amplifier means 44 for measuring light transmittance or absorption. The transmittance or the absorption of the monochromatic light after it passes through the colored complex is detected by said detector and amplifier means which determines a detector value proportionate to the transmittance or absorption of the light. The detector value is amplified by a suitable amplifying means and the value is readable on an indicating dial 45. The detector value is compared with a detector value measured on a standard sample treated similarly and as corrected by a blank sample to determine the nickel content of the chemical plating solution.

In general, the nickel analysis device of this invention is depending on the following chemical reactions and operations: The nickel plating solution is reacted with the ammonium hydroxide solution to produce a blue to violet colored complex, which is proportional in intensity to the amount of nickel present. The intensity of the colored solution is determined by measuring with a detector the transmittance or absorbance of the light that has passed through the test solution. The current from the detector is amplified and registered on an indicating dial of an appropriate meter. This reading is compared with the readings from the standard solutions of known concentration of nickel in them. From the calibration curve of the standard solutions, the concentration of nickel in the sample plating solution can be found.

The nickel analysis device operates in the following manner: A sample of plating solution is pumped into the first volumetric cup inner section 23 by a mechanical pump or a hand pump 21. The cup will hold only a predetermined volume, such as for example, 1,2,3, or more ml. The excess will be caught by the first volumetric cup outer section 25 which has a drain 26 at the bottom to return the excess to the plating tank container. A good practice includes pumping the plating solution through the tube for a few seconds to clean the tube, before pumping the plating solution into the first volumetric cup inner section 23. Then the sample plating solution is drained into the rectangular absorption cell below by turning on the stopcock 24 at the bottom stem of the first volumetric cup inner section 23. The volume of the rectangular absorption cell 41 can be for example, 50 ml, 100 ml or other values. Next the ammonium hydroxide solution is run into the second volumetric cup inner section 33 from the storage container for the standard ammonium hydroxide 31 by opening the valve at the bottom of the bottle. The second volumetric cup inner section 33 has also a predetermined volume, for example, 50 ml, 100 ml or other volumes. The volume of the second volumetric cup inner section 33 depends on the quantity of the sample of nickel used in the analysis. For a good result, the reacted ammonium hydroxide solution should contain about 1000 parts (with plus or minus of a few hundred parts) of nickel per million parts (PPM) of solution. The predetermined volume of 20% ammonium hydroxide solution (made from concentrated ammonium hydroxide of 0.90 density and 30% ammonia) is determined by the predetermined volume of chemical plating solution used, taking into account the acidity of the plating solution. The nickel plating solution is acidic and part of the ammonium hydroxide solution used in the reaction, is to neutralize the acid. The final solution in the absorption cell should contain excess ammonium hydroxide. The overflowing ammonium hydroxide solution from the second volumetric cup inner section 33 is caught by the second volumetric cup outer section 34; however, flows out can be diverted automatically to an ammonium hydroxide storage container or to waste, if desired. The ammonium hydroxide solution in the second volumetric cup inner section 33 is emptied into the rectangular absorption cell 41 through the stopcock 35 on the bottom stem of the cup inner section 33.

The test solution in the rectangular absorption cell 41 is stirred with a stirring rod to mix well. A complex color proportionate to the nickel content is to be measured for transmittance or absorption by a colorimeter. The colorimetric unit of the device is then turned on. The light from the tungsten lamp 43 will pass through the yellow filter 42 (near 580 millimicrons wavelength) to give a monochromatic light for a maximum absorption by the test solution. The transmittance of the absorption of the monochromatic light after it has passed through the violet solution is detected by the detector 44. The current from the detector is then amplified and the value is readable on the indicating scale 45. A green filter (near 525 millimicrons wavelength) can be employed in place of the yellow filter for sample and standard.

The specification of the formulation of the nickel plating solution generally states that there must be an upper limit and a lower limit to the amount of nickel in the plating solution. For example, one specification states that there must be between 7.5 and 10.0 ounces of nickel per gallon of plating solution. In making up the standard solutions, it is a good practice to make one solution representing the upper limit of the amount of nickel in the plating solution and another one representing the lower limit of the amount of nickel in the same solution. When the operator takes a reading from his analysis, he will know immediately whether his nickel plating solution is still within the specification.

When the standard solutions are made up, such solutions must contain the same constituents and in the same amount as in the plating solution, in order to eliminate the error in the transmittance or absorption measurement. For example, if the sample plating solution contains 5 ounces of boric acid per gallon of solution, the standard solutions must contain 5 ounces of boric acid per gallon of solution also. The standard solutions, if kept in glass stopped Pyrex bottles and in a cool place, will be stable as long as a year. A standard strength of ammonium hydroxide solution should be used when preparing the standard and the sample plating solutions. The colorimeter measurement system of the nickel analysis device must be standardized at least once a week. The colorimeter unit can be purchased on the open market, and should be equivalent to the colorimeter, catalog number, 7-103, in the catalog 70M of the Fisher Scientific Company, 711 Forbes Ave., Pittsburgh, PA 15219.

I claim:

1. A device for colorimetric analysis of nickel in an acidic chemical plating solution comprising: an automatic measuring system having a first and second automatic measuring system, said first measuring system having a container for holding acidic chemical plating solution, pumping means having an inlet and outlet member, said inlet member connected to said container for receiving said solution, a volumetric cup disposed to receive said solution discharged from said outlet member of said pump, said cup having an inner and an outer section, said inner section being connected to a first means for draining said solution, said outer section disposed for receiving any overflow from said inner section and means connecting said outer cup to said container; said second automatic measuring system having a second container for holding standardized ammonium hydroxide solution and positioned so that flow of said standardized ammonium hydroxide solution is gravity fed, a second volumetric cup having an inner and outer section, means for flow control connected between said second container and said cup, said inner section of said cup being disposed to receive said standardized ammonium hydroxide solution from said second container, said inner section of said cup having drain means at bottom for draining said standardized ammonium hydroxide solution, said outer section being disposed for receiving any overflow from said inner section and means connecting said outer section to an overflow container for receiving any overflow; a colorimeter measuring system having an absorption cell for receiving a desired solution from said first and second cups, a filter positioned adjacent to said cell, a lamp for providing a source of light positioned adjacent to said filter for receiving and transmitting said source of light, said filter yielding a monochromatic light, near the 580 millimicrons wavelength when said filter is a yellow filter or near 525 millimicrons wavelength when said filter is a green filter, which is transmitted through said absorption cell, a detector and amplifier means positioned on the side of the cell opposite said filter and in line with said light, and an indicator attached to said detector for indicating the amount of light received by said detector through said filter and said cell wherein the nickel content of said chemical plating solution is determined by comparison with detector indication of the amount of said light transmitted through a standard sample.

2. The device for use in the colorimetic analysis of nickel in an acidic chemical plating solution of claim 1 wherein said first volumetric cup outer section drain means automatically drains said overflow into said chemical plating solution tank container and wherein said second volumetric cup outer section drain means automatically drains said overflow into an overflow container for a standardized ammonium hydroxide solution.

* * * * *